US 6,773,409 B2
United States Patent
Truckai et al.

(10) Patent No.: US 6,773,409 B2
(45) Date of Patent: *Aug. 10, 2004

(54) SURGICAL SYSTEM FOR APPLYING ULTRASONIC ENERGY TO TISSUE

(75) Inventors: Csaba Truckai, Saratoga, CA (US);
John H. Shadduck, Tiburon, CA (US);
Bruno Strul, Portola Valley, CA (US)

(73) Assignee: SURGRx LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/957,529

(22) Filed: Sep. 19, 2001

(65) Prior Publication Data

US 2003/0055417 A1 Mar. 20, 2003

(51) Int. Cl.[7] ............................................. A61B 18/04
(52) U.S. Cl. ............................. 601/2; 601/3; 606/27; 606/28; 606/29; 606/49; 606/50; 606/51; 606/52
(58) Field of Search ..................... 601/2, 3; 606/27, 606/28, 29, 49, 50, 51, 52, 169

(56) References Cited

U.S. PATENT DOCUMENTS

| | | | |
|---|---|---|---|
| 659,409 | A | 10/1900 | Mosher |
| 1,586,645 | A | 6/1926 | Bierman |
| 1,798,902 | A | 3/1931 | Raney |
| 1,881,250 | A | 10/1932 | Tomlinson |
| 2,031,682 | A | 2/1936 | Wapplet at al. |

(List continued on next page.)

FOREIGN PATENT DOCUMENTS

| | | |
|---|---|---|
| EP | 341 446 A2 | 4/1989 |
| EP | 517 244 B1 | 3/1996 |
| EP | 518 230 B1 | 5/1996 |
| FR | 2536924 A1 | 6/1984 |
| FR | 2647683 A1 | 12/1990 |
| GB | 2037167 A | 7/1980 |
| GB | 2066104 A | 7/1981 |

(List continued on next page.)

OTHER PUBLICATIONS

Carson, S.L., "Two new laparoscopic instruments: Bipolar sterilizing forceps and uterine manipulator," *Medical Instrumentation*, 11(1):7–8 (1977).

Burton, J.D.K., "New Inventions," *The Lancet*, pp. 650–651 (1959).

Nardella, P.C., "Radio Frequency Energy and Impedance Feedback," *Proc. SPIE, Catheter–Based Sensing and Imaging Technology*, 1068: 42–48 (1989).

Vallfors et al., "Automatically controlled bipolar electrocoagulation—'COA–COMP'," *Neurosurg Rev.*, 187–190 (1984).

*Primary Examiner*—Michael Peffley
*Assistant Examiner*—Aaron Roane
(74) *Attorney, Agent, or Firm*—Townsend and Townsend and Crew LLP

(57) ABSTRACT

A surgical system for controlled application of ultrasound energy to engaged tissue volumes for creating effective biological welds or seals in tissue. The invention provides an ultrasound transmission assembly including piezoelectric elements coupled to an elongate waveguide that is reciprocatable in an interior of an introducer. The reciprocatable waveguide assembly of the invention is adapted to have multiple functionality: (i) to couple ultrasound energy to both opposing jaws to thereby deliver energy to both sides of engaged tissues to create uniform thermal weld effects; (ii) to apply very high compressive forces to captured tissues over the length of elongate jaws by engaging substantially the entire length of the jaws, and (iii) to transect the captured tissues contemporaneous with the delivery of energy to create the thermal weld. The invention further provides for use of other energy sources to deliver thermal energy to tissue, for example microwave energy, Rf energy and laser energy, either in combination with ultrasound energy or independently.

17 Claims, 11 Drawing Sheets

U.S. PATENT DOCUMENTS

| | | |
|---|---|---|
| 3,651,811 A | 3/1972 | Hildebrandt et al. |
| 3,685,518 A | 8/1972 | Beuerle et al. |
| 3,730,188 A | 5/1973 | Ellman |
| 3,768,782 A | 10/1973 | Shaw |
| 3,826,263 A | 7/1974 | Cage et al. |
| 4,092,986 A | 6/1978 | Schneiderman |
| 4,198,957 A | 4/1980 | Cage et al. |
| 4,219,025 A | 8/1980 | Johnson |
| 4,231,371 A | 11/1980 | Lipp |
| 4,232,676 A | 11/1980 | Herczog |
| 4,271,838 A | 6/1981 | Lasner et al. |
| 4,353,371 A | 10/1982 | Cosman |
| 4,370,980 A | 2/1983 | Lottick |
| 4,375,218 A | 3/1983 | DiGeronimo |
| 4,492,231 A | 1/1985 | Auth |
| 4,590,934 A | 5/1986 | Malis et al. |
| 4,608,981 A | 9/1986 | Rothfuss et al. |
| 4,633,874 A | 1/1987 | Chow et al. |
| 4,655,216 A | 4/1987 | Tischer |
| 4,671,274 A | 6/1987 | Sorochenko |
| 4,691,703 A | 9/1987 | Auth et al. |
| 4,763,669 A | 8/1988 | Jaeger |
| 4,785,807 A | 11/1988 | Blanch |
| 4,848,337 A | 7/1989 | Shaw et al. |
| 4,850,353 A | 7/1989 | Stasz et al. |
| 4,887,612 A | 12/1989 | Esser et al. |
| 4,940,468 A | 7/1990 | Petillo |
| 4,958,539 A | 9/1990 | Stasz et al. |
| 4,969,885 A | 11/1990 | Farin |
| 4,985,030 A | 1/1991 | Melzer et al. |
| 5,009,656 A | 4/1991 | Reimels |
| 5,057,106 A | 10/1991 | Kasevich et al. |
| 5,057,107 A | 10/1991 | Parins et al. |
| 5,085,659 A | 2/1992 | Rydell |
| 5,104,025 A | 4/1992 | Main et al. |
| 5,122,137 A | 6/1992 | Lennox |
| 5,147,356 A | 9/1992 | Bhatta |
| 5,147,357 A | 9/1992 | Rose et al. |
| 5,151,102 A | 9/1992 | Kamiyama et al. |
| 5,190,541 A | 3/1993 | Abele et al. |
| 5,201,900 A | 4/1993 | Nardella |
| 5,207,691 A | 5/1993 | Nardella |
| 5,258,006 A | 11/1993 | Rydell et al. |
| 5,267,998 A | 12/1993 | Hagen |
| 5,269,780 A | 12/1993 | Roos |
| 5,290,286 A | 3/1994 | Parins |
| 5,306,280 A | 4/1994 | Bregen et al. |
| 5,308,311 A | 5/1994 | Eggers et al. |
| 5,324,289 A | 6/1994 | Eggers |
| 5,336,221 A * | 8/1994 | Anderson ............ 606/27 |
| 5,360,428 A | 11/1994 | Hutchinson, Jr. |
| 5,364,389 A | 11/1994 | Anderson |
| 5,389,098 A | 2/1995 | Tsuruta et al. |
| 5,403,312 A | 4/1995 | Yates et al. |
| 5,417,687 A | 5/1995 | Nardella et al. |
| 5,443,463 A | 8/1995 | Stern et al. |
| 5,445,638 A | 8/1995 | Rydell et al. |
| 5,451,224 A | 9/1995 | Goble et al. |
| 5,458,598 A | 10/1995 | Feinberg et al. |
| 5,480,397 A | 1/1996 | Eggers et al. |
| 5,480,398 A | 1/1996 | Eggers |
| 5,507,106 A | 4/1996 | Fox |
| 5,531,744 A | 7/1996 | Nardella et al. |
| 5,571,153 A | 11/1996 | Wallsten |
| 5,573,535 A | 11/1996 | Viklund |
| 5,593,406 A | 1/1997 | Eggers et al. |
| 5,611,798 A | 3/1997 | Eggers |
| 5,624,452 A | 4/1997 | Yates |
| 5,674,220 A | 10/1997 | Fox et al. |
| 5,693,051 A | 12/1997 | Schulze et al. |
| 5,716,366 A | 2/1998 | Yates |
| 5,735,848 A | 4/1998 | Yates et al. |
| 5,755,717 A | 5/1998 | Yates et al. |
| 5,766,166 A | 6/1998 | Hooven |
| 5,776,130 A | 7/1998 | Buysse et al. |
| 5,797,938 A | 8/1998 | Paraschac et al. |
| 5,800,449 A | 9/1998 | Wales |
| 5,807,392 A | 9/1998 | Eggers |
| 5,833,690 A | 11/1998 | Yates et al. |
| 5,911,719 A | 6/1999 | Eggers |
| 5,947,984 A * | 9/1999 | Whipple ............ 606/151 |
| 6,019,758 A | 2/2000 | Slater |
| 6,039,733 A | 3/2000 | Buysse et al. |
| 6,074,389 A | 6/2000 | Levine et al. |
| 6,086,586 A | 7/2000 | Hooven |
| 6,113,598 A * | 9/2000 | Baker ............ 606/51 |
| 6,139,508 A | 10/2000 | Simpson et al. |
| 6,152,923 A | 11/2000 | Ryan |
| 6,162,220 A | 12/2000 | Nezhat |
| 6,174,309 B1 | 1/2001 | Wrublewski et al. |
| 6,176,857 B1 | 1/2001 | Ashley |
| 6,179,834 B1 | 1/2001 | Buysse et al. |
| 6,179,835 B1 | 1/2001 | Panescu et al. |
| 6,179,837 B1 | 1/2001 | Hooven |
| 6,187,003 B1 | 2/2001 | Buysse et al. |
| 6,190,386 B1 | 2/2001 | Rydell |
| 6,193,709 B1 * | 2/2001 | Miyawaki et al. ............ 606/49 |
| 6,270,497 B1 | 8/2001 | Sekino et al. |
| 6,273,887 B1 | 8/2001 | Yamauchi et al. |
| 6,277,117 B1 | 8/2001 | Tetzlaff et al. |
| 6,293,946 B1 * | 9/2001 | Thorne ............ 606/48 |
| 6,296,640 B1 | 10/2001 | Wampler et al. |
| 6,328,703 B1 * | 12/2001 | Murakami ............ 601/4 |
| 6,334,861 B1 | 1/2002 | Chandler et al. |
| 6,350,264 B1 | 2/2002 | Hooven |
| 6,352,536 B1 | 3/2002 | Buysse et al. |
| 6,398,779 B1 | 6/2002 | Buysse et al. |
| 6,409,725 B1 | 6/2002 | Khandkar et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,704 B2 | 10/2002 | Schmaltz et al. |
| 6,468,275 B1 | 10/2002 | Wampler et al. |
| 6,500,176 B1 | 12/2002 | Truckai et al. |
| 6,511,480 B1 | 1/2003 | Tetzlaff et al. |
| 6,527,767 B2 | 3/2003 | Wang et al. |
| 6,533,784 B2 | 3/2003 | Truckai et al. |
| 6,554,829 B2 | 4/2003 | Schulze et al. |
| 6,575,968 B1 | 6/2003 | Eggers et al. |
| 6,585,735 B1 | 7/2003 | Frazier et al. |
| 6,632,193 B1 | 10/2003 | Davison et al. |
| 6,652,521 B2 | 11/2003 | Schulze |
| 2002/0052599 A1 | 5/2002 | Goble |
| 2002/0115997 A1 * | 8/2002 | Truckai et al. ............ 606/51 |
| 2002/0120266 A1 | 8/2002 | Truckai et al. |
| 2002/0169392 A1 | 11/2002 | Truckai et al. |
| 2002/0177848 A1 | 11/2002 | Truckai et al. |
| 2003/0018327 A1 | 1/2003 | Truckai et al. |
| 2003/0050635 A1 | 3/2003 | Truckai et al. |
| 2003/0055417 A1 | 3/2003 | Truckai et al. |
| 2003/0069579 A1 | 4/2003 | Truckai et al. |
| 2003/0078573 A1 | 4/2003 | Truckai et al. |
| 2003/0078577 A1 | 4/2003 | Truckai et al. |
| 2003/0078578 A1 | 4/2003 | Truckai et al. |
| 2003/0114851 A1 | 6/2003 | Truckai et al. |
| 2003/0125727 A1 | 7/2003 | Truckai et al. |
| 2003/0139741 A1 | 7/2003 | Goble et al. |
| 2003/0144652 A1 | 7/2003 | Baker et al. |

FOREIGN PATENT DOCUMENTS

| | | |
|---|---|---|
| GB | 2133290 A | 7/1984 |

| | | | | | |
|---|---|---|---|---|---|
| GB | 2161082 A | 1/1986 | WO | WO 94/24949 A1 | 11/1994 |
| SU | 575103 | 10/1977 | WO | WO 94/24951 A1 | 11/1994 |
| SU | 342617 | 12/1980 | | | |
| WO | WO 93/08754 A1 | 5/1993 | * cited by examiner | | |

SURGICAL SYSTEM FOR APPLYING ULTRASONIC ENERGY TO TISSUE

CROSS-REFERENCE TO RELATED APPLICATIONS

This application is related to co-pending U.S. patent application Ser. No. 09/792,825 filed Feb. 24, 2001 titled Electrosurgical Working End for Transecting and Sealing Tissue, which is incorporated herein by this reference.

BACKGROUND OF THE INVENTION

1. Field of the Invention

The present invention relates to surgical instruments with paired jaws that deliver thermal energy to the engaged tissues to create an effective seal or weld in the tissue. More in particular, the invention applies extremely high compressive forces to engaged tissue together with the application of ultrasonic energy to the tissue from two opposing sides of the tissue to thereby effectively deliver energy to the tissue.

2. Background of the Invention

In various open and laparoscopic surgeries, it is necessary to seal or weld the tissue volumes targeted for transection. Many common procedures require both sealing and transection of tissue, for example, the take-down of gastric arteries in endoscopic Nissen fundoplications, the sealing of tissue margins in lung resections, and the sealing of blood vessels in endoscopic colon surgeries that transect the mesentery. In some such procedures, stapling instruments are used to apply a series of mechanically deformable staples to transected blood vessels or other tissue volumes. The use of such mechanical is time consuming and often will not create an effective seal resulting in leaks that can cause serious complications.

Surgical instruments that utilize ultrasound energy for coagulating, sealing or transecting tissue have been commercialized for use in both open and endoscopic procedures. The ultrasonic instruments that are available suffer from several disadvantages. A typical prior art ultrasonic instrument has (i) a rigid energy-transmitting member that transmits acoustic vibrations from the handle to the working end, and (ii) a moveable jaw member that is used to capture and press the targeted tissue volume against the single energy-transmitting member. (See, e.g., U.S. Pat. No. 5,322,055).

It has been found that prior art ultrasound instruments cannot apply significant compressive forces against tissues to create a reliable, effective weld in many targeted tissues—particularly in (i) substantially thick anatomic structures; (ii) large diameter blood vessels; (iii) tissue volumes that are not uniform in hydration, density and collagenous content; and (iv) bundles of disparate anatomic structures. It also has been found that prior art ultrasound instruments are inefficient at delivering energy to the above-described targeted tissues since the energy is only delivered from one surface of the engaged tissue. A further disadvantage of commercially available ultrasound instruments is that they cannot easily be reduced in cross-sectional dimension—which would be useful for less invasive surgeries. The typical prior art instrument has a first elongate energy-transmitting member that extends the length of the instrument plus a second adjacent extension member that comprises linkage for opening and closing the jaw structure. Another disadvantage of prior art ultrasound instruments in lack of functionality with respect to transecting tissue and welding the tissue volume. Typically, the instrument requires reconfiguration of the working end in order to first perform a sealing task and then to perform a transection task, which is inconvenient and time-consuming.

SUMMARY OF THE INVENTION

The present invention relates to a surgical instrument that is adapted to transect a targeted tissue volume and contemporaneously weld the margins of the transected tissue. As background, the biological mechanisms underlying tissue fusion by means of thermal effects are not fully understood. In general, the delivery of energy for sealing a targeted tissue volume—no matter the source—is adapted to denature proteins, including collagen, into a proteinaceous amalgam that intermixes and fuses together as the proteins renature. As the treated region heals over time, the damaged tissue is partly reabsorbed by the body's wound healing process resulting in a scar-type tissue or biological weld. In order to create an effective weld in tissue volumes that are not uniform in hydration or collagen content, such as blood vessels with significant fascia layers, it has been found that several factors are critical. First, it has been found that the application of very high compressive forces to the engaged tissue prior to, or contemporaneous with, energy delivery can greatly increase the strength of the weld. It is believed that such very high compressive forces cause more effective entanglement and intermixing of denatured proteins thereby increasing the strength and uniformity of the developing biological weld. It has further been found that effective welds require a uniform selected temperature across the targeted tissue volume for a selected time interval. The working end of the invention utilizes high compressive forces to homogenize the engaged tissue by causing extracellular fluids to migrate away from the engaged tissue to collateral regions to create uniform hydration. In other words, the energy absorption characteristics of the engaged tissue can be made more uniform to allow a more even temperature distribution across the targeted tissue volume to thereby create a uniform weld.

One preferred embodiment of the invention provides an improved system of coupling ultrasound energy to engaged tissue volumes to weld tissue. More in particular, the invention provides an ultrasound transmission unit and elongate waveguide that is reciprocatable in an interior bore of an introducer. Unlike prior art ultrasound instruments, the waveguide of the present invention is not adapted to directly engage tissue. Instead, the elongate waveguide of the invention carries channels with engagement surfaces therein that are adapted to continuously engage cooperating exterior surfaces of first and second jaw elements under very close tolerances. The invention thus provides first and second jaw elements that are part of a tuned acoustic assembly wherein acoustic wave transmission is coupled between the waveguide and the jaws. Thus, the reciprocatable waveguide of the invention is adapted to perform several unique functions: (i) to couple ultrasound energy to both opposing jaws to thereby deliver energy to both sides of the captured tissue to create uniform thermal weld effects; (ii) to apply very high compressive forces to the captured tissue by having the reciprocating member engage the jaws substantially along the entire length of the jaws, and (iii) to transect the captured tissue contemporaneously with the delivery of energy that is adapted to weld the tissue.

Of particular interest, the invention allows the reciprocatable ultrasonic transmission assembly to be easily sterilizable and reusable since it does not directly contact tissues. Such a reusable ultrasonic transmission assembly then can be inserted in a disposable handle-introducer that carries a jaw structure that actually engages the tissue. Further, the use of the reciprocatable ultrasonic transmission assembly as a mechanism for actuating the jaw structure between open and closed positions allows the cross-section of the working end to be scaled down in dimension for less invasive surgeries—that would not be possible with prior art designs of ultrasound instruments.

In general, the apparatus and method of the present invention advantageously provide means for effectively coupling ultrasonic energy to engaged tissue for purposes of welding tissue.

The present invention advantageously provides a system that allows for ultrasonic energy transmission to both opposing jaw faces of a working end that engages tissue under high compression.

The present invention provides an ultrasonic energy transmission unit that is independent of the opposing jaw surfaces that engage and compress tissue.

The present invention provides a reciprocating ultrasonic energy transmission unit that slidably mates with independent first and second jaw elements that are a part of the tuned acoustic assembly.

The present invention provides a reciprocatable ultrasonic energy transmission unit that is reusable and is adapted for used with a disposable introducer-jaw assembly.

The present invention provides an ultrasonic energy transmission assembly that is reciprocatable with very close tolerances over an independent jaw assembly to provide combined functionality: (i) to deliver ultrasonic energy to the working end, and (ii) to open and close the jaw elements.

The present invention provides an ultrasonic energy transmission unit that can be fabricated in single member to without moving parts that can effectively transmit ultrasonic energy to opposing first and second openable-closeable jaw elements.

The present invention provides a system that can scale the ultrasonic energy transmission unit small diameters when compared to prior art devices.

The present invention provides a reusable ultrasonic energy transmission unit that can be easily fitted with a disposable sharp blade for transecting tissue.

The present invention provides a system for applying extreme compressive forces on capture tissue volume to reduce the tissue cross-section to about 0.001" to insure uniform energy densities for effective tissue welding.

The present invention provides an ultrasonic energy delivery system that can prevent tissue ablation or desiccation due to excess thermal energy delivery.

Additional objects and advantages of the invention will be apparent from the following description, the accompanying drawings and the appended claims.

DETAILED DESCRIPTION OF THE INVENTION

Figure 1:
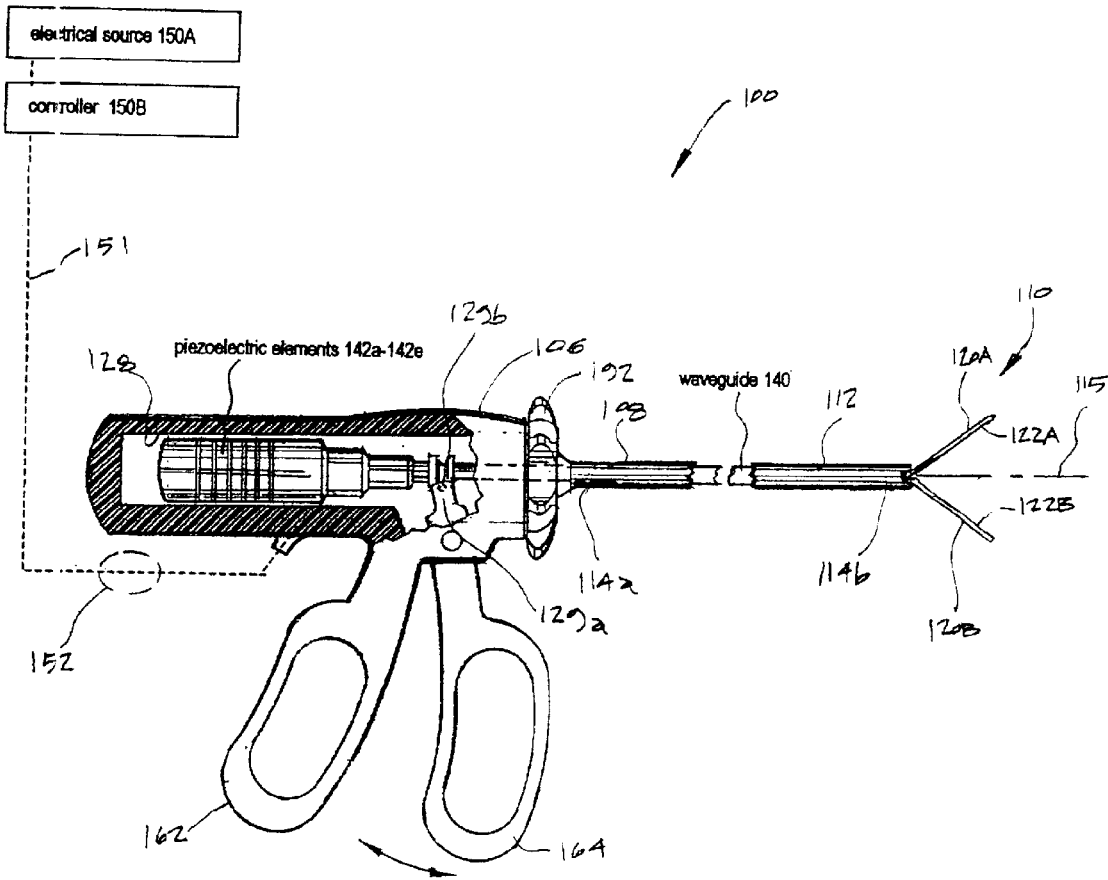
FIG. 1 is a Type "A" system of the invention with a partly sectional view of a handpiece and working end that carry a reciprocatable ultrasonic transducer assembly coupled to a remote electrical source.

1. Type "A" system for sealing and transecting tissue. Referring to FIG. 1, an exemplary Type "A" instrument system 100 is shown having a device handle portion 106 and elongate introducer portion 108 carrying a distal working end 110 that is adapted to engage a targeted tissue volume. Effective tissue welding can be accomplished by a combination of: (i) methods for capturing targeted tissue under extreme compressive forces between opposing tissue-contacting surfaces to provide a substantially uniform, very thin tissue cross-section for welding, and (ii) methods for controlled delivery of ultrasonic energy to the captured tissue from the tissue-contacting surfaces on both sides of the tissue to maintain the highly-compressed tissues within a substantially narrow temperature range for selected time interval.

The present invention is directed to multiple aspects of instrument system 100 that are adapted to transect and seal or weld tissue. The first described aspect of the invention is directed to means for coupling ultrasonic energy to both first and second opposing tissue-contacting jaw faces wherein the jaws are part of the tuned acoustic assembly. The second described aspect of the invention is directed to the features of the working end 110 that provide for tissue engagement under extremely high compressive forces. With reference to FIGS. 1–4, the working end 110 of the instrument 100 also is adapted for tissue cutting as will be described below. Further, the working end 110 is configured for general tissue clamping and manipulating purposes in a surgical procedure without utilizing the tissue welding and transecting aspects of the invention. The present invention thus is adapted for use in open surgical procedures as well as endoscopic procedures.

Figure 2:
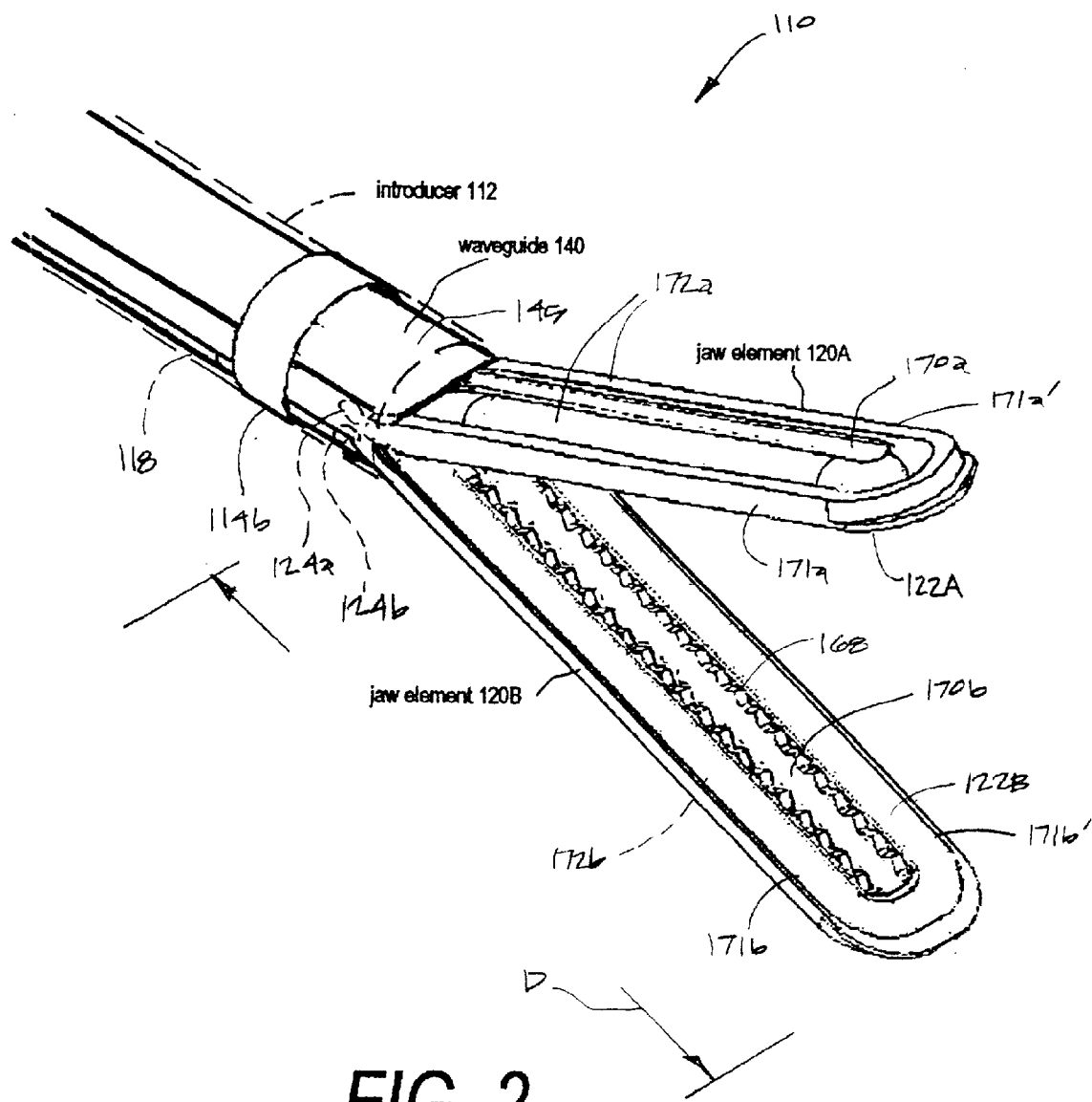
FIG. 2 is an enlarged perspective view of the working end of the system of FIG. 1 with the jaw elements in a first open position and the reciprocating waveguide member in a first retracted position.

With reference to FIGS. 1 and 2, an exemplary instrument is shown with introducer sleeve 112 having proximal end 114a and distal end 114b. The sleeve 112 extends along longitudinal axis 115 and comprises a thin-wall tubular sleeve with bore or passageway 118 extending therethrough. As will be described in detail below, paired first and second elongate jaw elements 120A and 120B that define jaw faces or planes 122A and 122B are pivotably coupled to the distal portion of introducer sleeve 112. In one embodiment, the paired jaw elements have pin portions indicated at 124a and 124b that cooperate with receiving bores in introducer sleeve 112 to thus allow the jaw elements to pivotably move between a first open position and a second closed (or approximated) position (see FIG. 2).

Figure 3:
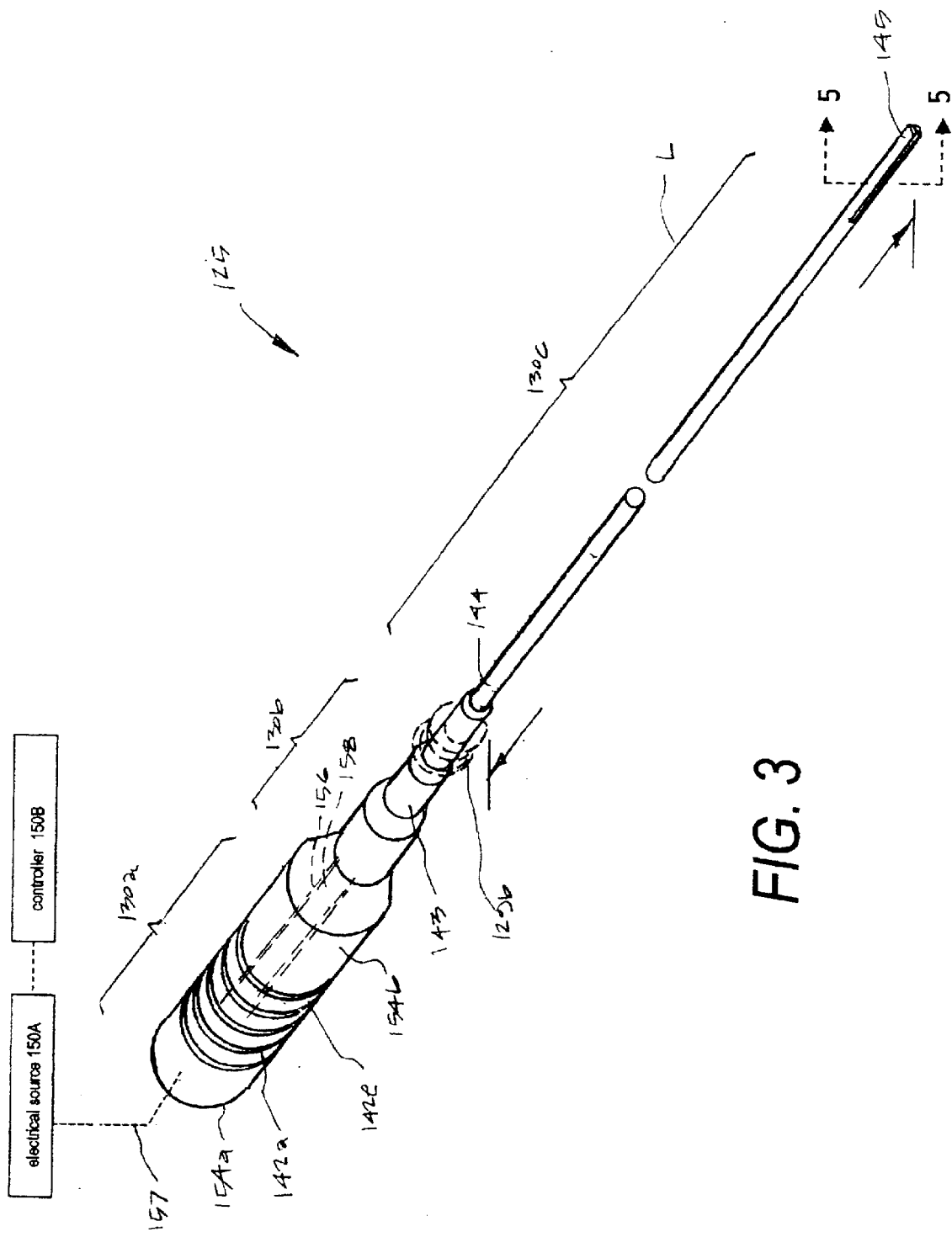
FIG. 3 is a perspective view of the reciprocatable ultrasonic energy transmission assembly of the invention de-mated from the hand piece of FIG. 1.

Now turning to FIGS. 1 and 3, particular aspects of the ultrasonic energy transmission unit or assembly 125 of the instrument system will be described. Of particular interest, the instrument provides an ultrasonic energy transmission assembly 125 that is reciprocatable within a chamber or bore 128 in the handle housing that communicates with the aligned, cooperating bore 118 within introducer sleeve 112. With reference to FIGS. 1 and 3, it can be seen that a reciprocating movement of ultrasonic assembly 125 is effected by yoke end portion 129a of a lever arm of handle 106 that engages a drive collar 129b of unit 125. The handle portion 106 that carries the ultrasonic transmission unit 125 of the instrument can comprise mating housings that are adapted to isolate the physician from the vibrations of ultrasonic assembly 125. The diameter of tubular sleeve 112 may range from about 2.0 mm. to 6.0 mm., although larger diameter sleeves fall within the scope of the invention.

In one preferred embodiment, the ultrasonic energy transmission assembly 125 of FIG. 3 can be reusable and removable from the interior of a disposable introducer portion and jaw structure. It can easily be understood how the ultrasonic unit 125 can be sterilized for reuse—since the distal end of the unit 125 does not directly engage tissue. Thus, the handpiece portion and tissue-engaging jaws can be inexpensive and disposable. It should be appreciated that the instrument also can be configured for disposable use, wherein the jaw elements are non-detachably integrated with the ultrasonic transmission component of the invention.

Figure 7:
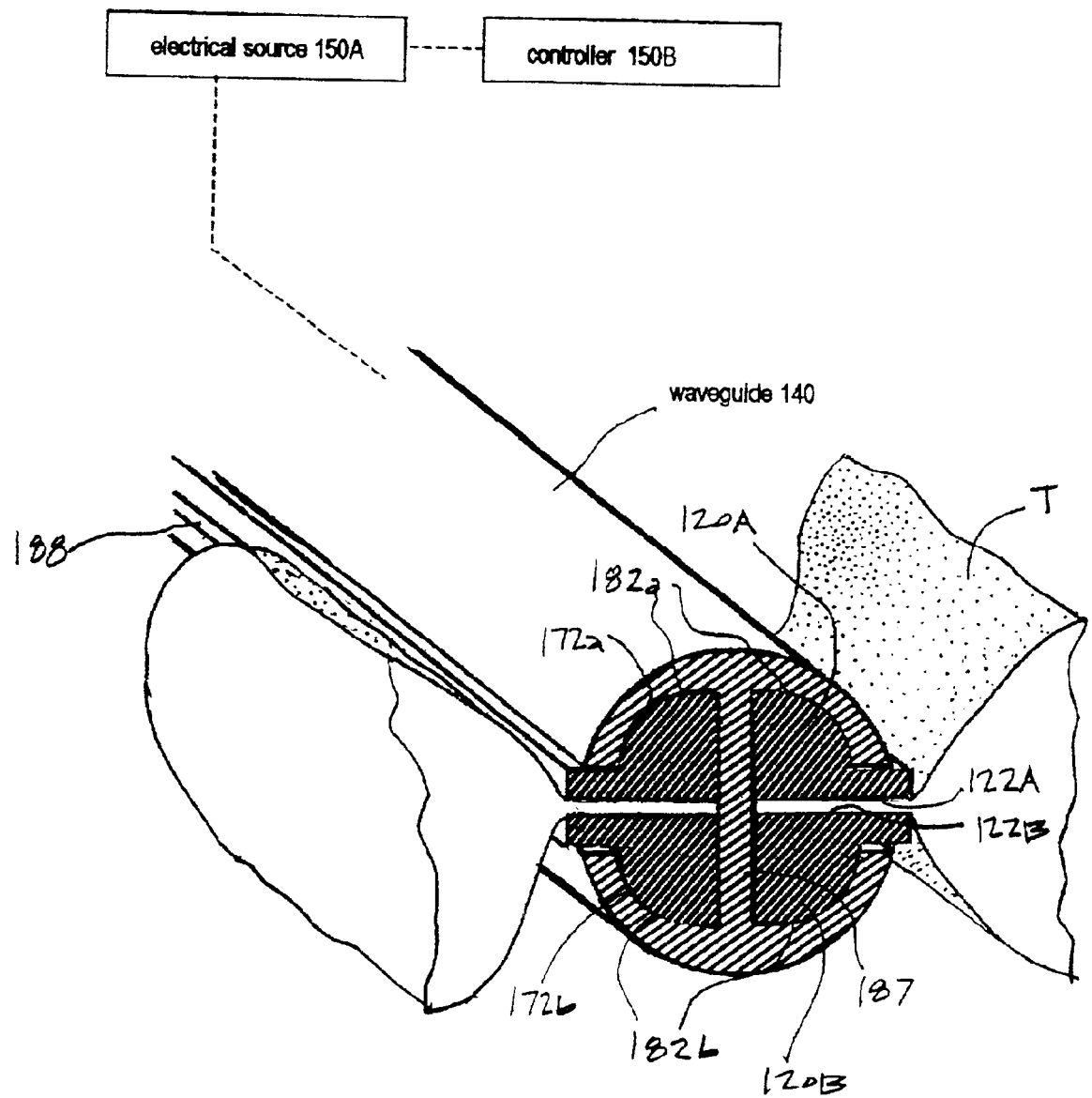
FIG. 7 is a sectional view of the waveguide and jaw elements engaging tissue in FIG. 6.

The ultrasonic transmission unit or assembly 125 generally includes a proximal (first) ultrasonic portion 130a, a medial (second) ultrasonic portion 130b and a terminal (third) portion indicated at 130c (see FIG. 3). The first ultrasonic portion comprises the transducer (energy transduction) components of the invention. The second or medial ultrasonic portion comprises an amplifier component and the third ultrasonic portion defines an extension member or waveguide 140. The waveguide 140 is multifunctional in that it is adapted (i) to slidably cooperate with the paired jaw elements to provide jaw opening-closing functionality, (ii) to mechanically couple a substantially elongate anti-node portion of the waveguide with a cooperating elongate length of the paired jaw elements in such a manner so as to efficiently transmit ultrasonic energy thereto thus making both jaws function as components of a tuned acoustic assembly, and (iii) to provide extremely rigid engagement surfaces that engage substantially the entire length of the jaw elements in such a manner so as to provide extremely high compressive forces on captured tissue. The cooperating slidable engagement surfaces of the reciprocating waveguide and jaw elements can have a part-round cross-section as shown in FIGS. 2 and 7, or planar surfaces or any plurality of mating grooves that can be optimized for making the jaws integral to the tuned acoustic assembly.

The components of the ultrasonic transmission unit 125 preferably are tuned acoustically as is known in the art to provide that the selected longitudinal vibration frequency is effective in delivering energy to the terminal portion 130c of the ultrasonic assembly 125 and thereafter to jaw elements 120A and 120B that actually engage the targeted tissue. The proximal portion 130a of the assembly, or transducer portion, preferably comprises at least one piezoelectric element, in this case elements 142a–142e, together with opposing polarity electrodes coupled to each piezoelectric element (not shown). The piezoelectric elements 142a–142e can be fabricated from a suitable material, for example, lead zirconate-titanate, or any other piezoelectric material. In use, the piezoelectric components of ultrasonic transmission assembly 125 convert an electrical signal into mechanical energy that results in a longitudinal vibratory motion of the shaft portion 143 of the medial assembly portion 130b and the waveguide or extension member 140.

When such an ultrasonic assembly 125 is energized, a vibratory motion in the form of a standing wave is generated throughout the length of the assembly 125, and in particular from the waveguide's proximal end 144 to its distal end portion 145. The propagation of such vibratory motion at particular points along the length of the ultrasonic assembly 125 depends on the exact longitudinal location at which the vibratory motion is measured. A minimum in the vibratory motion or standing wave is commonly referred to as a node, wherein motion is at minimal level. The location at which the vibratory motion reaches a peak in the standing wave is referred to as an anti-node, and the length L of the waveguide is selected to provide such anti-node characteristics generally within the distal end portion 145 of the waveguide 140.

An electrical source 150A and controller 150B are coupled to piezoelectric elements 142a–142e to drive or excite the ultrasonic assembly 125 at any suitable resonant frequency of the combination of components including the jaw elements of the tuned acoustic assembly. The electrical source 150A transmits an electrical signal through cable 151 to piezoelectric elements 142a–142e at a selected frequency and phase which is programmable by controller 150B. Typically, when the source 150A is actuated via a trigger mechanism 152, electrical energy is applied in a continuous period to the piezoelectric elements 142a–142e or transducer stack of the unit. The trigger 152 preferably comprises a foot-switch that is coupled to source 150A by a cable. Alternatively, the trigger 152 can be a finger switch incorporated in handle 106 to allow source 150A to be activated by the physician. The controller 150B also can monitor feedback signals from the ultrasonic transmission assembly 125 and can adjust the frequency of electrical energy sent by source 150A to match a resonant frequency of the selected longitudinal mode of vibration of the ultrasonic assembly including any load thereon as is known in the art.

More in particular, referring to FIG. 3, a first resonator portion 154a is connected to the proximal end of the transducer portion and a second resonator 154b is connected to the distal end of transducer portion. The first and second resonator portions preferably are fabricated of stainless steel, titanium, aluminum, or any other material that is well suited for acoustic wave transmission. These resonator portions have a length determined by a several variables, including the length and number of piezoelectric elements, the velocity of sound within the material from which the resonators are fabricated and the optimal frequency of the assembly 125. The second resonator 154b is coupled to shaft portion 143 that in this embodiment is stepped into reduced cross-section portions to function as an amplifier of the ultrasonic vibrations that are transmitted to waveguide 140. In one embodiment, the piezoelectric elements 142a–142e, and opposing polarity electrodes coupled thereto, are configured with a central bore 156 that carries a central shaft portion 158 that connects to first and second resonator portions 154a and 154b under high compression. The electrodes are electrically coupled to electrical source 150A by electrical leads 157 in the handle portion 106 of the instrument. The central shaft portion 158 is directly coupled to, or is unitarily formed with, shaft 143 that comprises the medial ultrasonic portion 130*b*.

In operation, the piezoelectric elements 142*a*–142*e* are energized in response to an electrical signal provided by source 150A to thereby produce an acoustic standing wave in the acoustic assembly 125 (FIG. 3). More in particular, the electrical signal creates an electromagnetic field within and across the plurality of piezoelectric elements 142*a*–142*e* thereby causing the elements to expand and contract in a continuous manner along an axis of the voltage gradient to produce high frequency longitudinal waves of ultrasonic energy. The ultrasonic energy is transmitted through the shaft 143 and thereafter through the entire length of waveguide 140.

In a preferred embodiment, the medial portion 130*b* preferably is configured to amplify the ultrasonic vibrations that are transmitted through the assembly 125 to the termination 145 of the waveguide 140. As shown in FIGS. 1 and 3, the shaft 143 of the medial ultrasonic unit 130*b* is of a solid material that comprises a stepped horn. As ultrasonic energy is transmitted through this medial portion 130*b*, the velocity of the acoustic wave transmitted is thus amplified. It is contemplated that the medial portion 130*b* be configured in a suitable shape known in the art, for example, a continuously tapered horn, a conical horn, etc. The proximal end 144 of waveguide 140 preferably is coupled to shaft portion 143 by an internal threaded connection proximate to the location of an anti-node of the assembly, or alternatively the shaft portion 143 and waveguide 140 can be unitarily fabricated.

Referring back to FIG. 1, it can be seen that a handle portion 106 of the instrument carries fixed grip 162 and a pivotable lever arm grip 164 that is adapted to reciprocate the waveguide-extension member 140 which in turn moves the jaw faces 122A and 122B between an open position and a closed position. Of particular interest, unlike prior art ultrasonic devices, the waveguide 140 of ultrasonic unit 125 is not adapted to contact the targeted tissue to thereby deliver energy to tissue (see FIGS. 6 and 7). Rather, the distal end of the waveguide-extension member 140 is coupled with very close tolerances to outer surfaces of jaw elements 120A and 120B that actually engage the targeted tissue and transfer ultrasonic energy to the tissue. As the jaw faces 122A and 122B engage tissue, the ultrasonic energy couples with the tissue and thermal energy is generated within the tissue as a result of acoustic absorption. This thermal energy then causes denaturation of proteins in the tissue to form a biological amalgam that under very high compressive pressures intermixes to form a weld and coagulum. Both microvessels and larger size vessels can be sealed by such energy delivery.

The electrical signal supplied to ultrasonic transmission unit 125 and more particularly to the distal termination 145 of waveguide 140 to cause longitudinal vibrations therein is preferably in the range of approximately 15 kHz to 500 kHz, and more preferably in the range of about 40 kHz to 100 kHz. Also, a feedback loop in controller 150B can maintain the electrical current supplied to the ultrasonic transmission unit 125 at a selected constant level to provide a substantially constant effect at the working end 110 of the device. For example, the propagation of vibrations to tissue at Or the working end can be controlled by the amplitude of the electrical signal applied to the piezoelectric assembly of the transmission unit 125.

Now turning to FIGS. 4–7, next described is the inventive apparatus and method for creating extremely high compressive forces between jaws elements 120A and 120B of the working end 110, as well as for effectively coupling the waveguide 140 to the jaw elements to cause the jaws to function as part of a tuned acoustic assembly. In one preferred embodiment, the jaw elements 120A and 120B are pivotably coupled to introducer sleeve 112 and each jaw element has a continuous uniform part-cylindrical cross-section (FIG. 2). It is the axial reciprocation of waveguide 140 in relation to jaws elements 120A and 120B that opens and closes the jaw faces 122A and 122B relative to axis 115 and provides further functionality, namely, (i) to cause the jaw's engagement surfaces 122A–122B to apply very high compressive forces on margins of tissue to be captured and transected; and (ii) to guide the distal end 145 of waveguide 140 that carries a sharp blade-type cutting element 166 (phantom view) along a targeted path p in tissue (see FIGS. 4, 5 and 7). Thus, the jaw elements and faces 122A and 122B are longitudinally positioned proximate to an anti-node when the waveguide is in an extended position so that the jaws couple with the tuned ultrasonic assembly to provide a preferred resonant frequency when the ultrasonic assembly is not loaded by tissue. When the transducer assembly is energized, the distal end 145 of waveguide 140 and jaw faces are configured to move longitudinally in the range of, for example, approximately 5–500 microns peak-to-peak at the selected vibrational frequency to thereby deliver energy to the engaged tissue.

In the exemplary embodiment of FIGS. 2 and 7, the elongate jaw elements 120A and 120B are fabricated in a part-round cross-section, for example, having a diameter ranging from about 0.03″ to 0.20″. The continuous cross-sections of jaw elements 120A and 120B define tissue-contacting surfaces (or planes) indicated at 122A–122B, respectively, that are can be flat but are shown with an inner edge having serrations or grip elements 168 to provide suitable tissue-gripping characteristics to the tissue engaging surfaces. In the exemplary embodiment of FIG. 2, the first and second jaw elements 120A and 120B define slots 170*a*–170*b* between left-side and right-side portions or each jaw, for example, indicated as sub-elements 171*a* and 171*a*' in jaw 120A and sub-element rods 171*b* and 171*b*' in jaw 120B.

Figure 4:
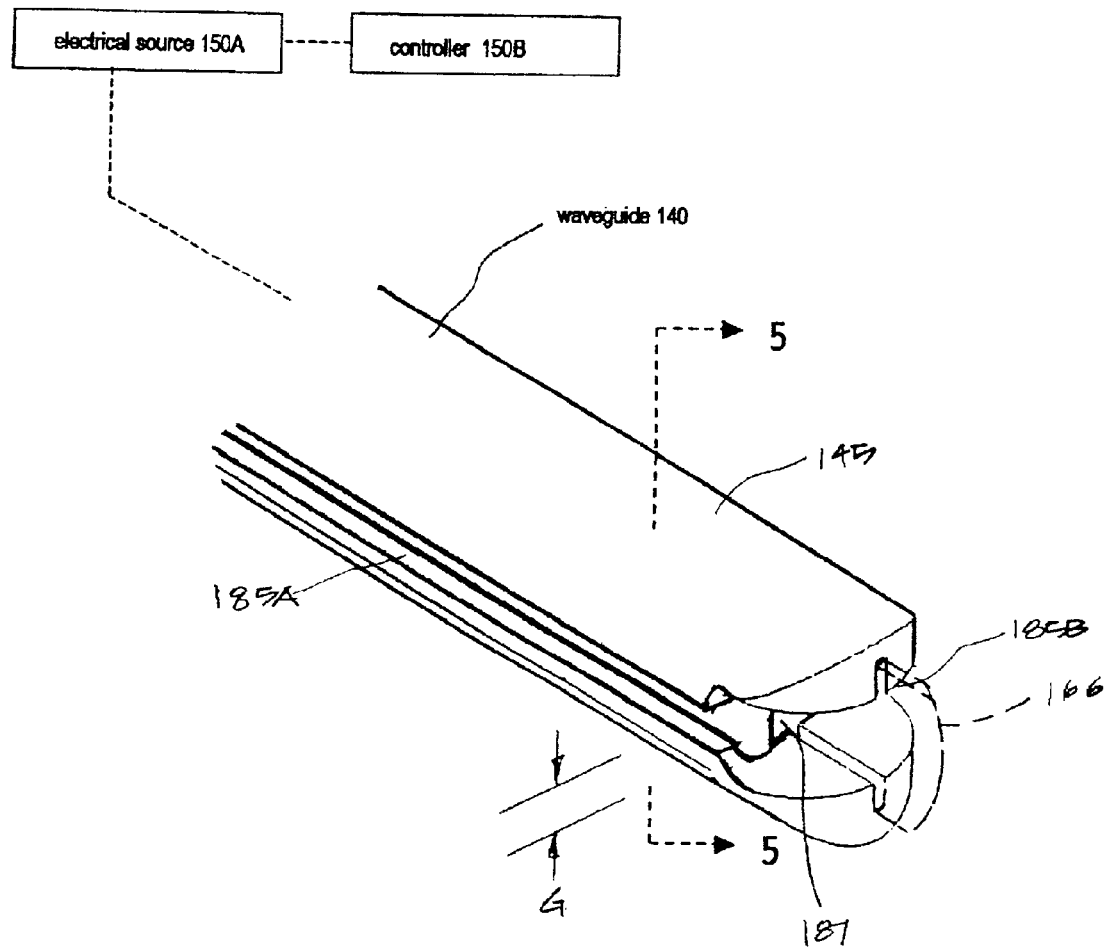
FIG. 4 is an enlarged perspective view of the distal end of the waveguide portion of the ultrasonic energy transmission assembly of FIG. 3.
Figure 5:
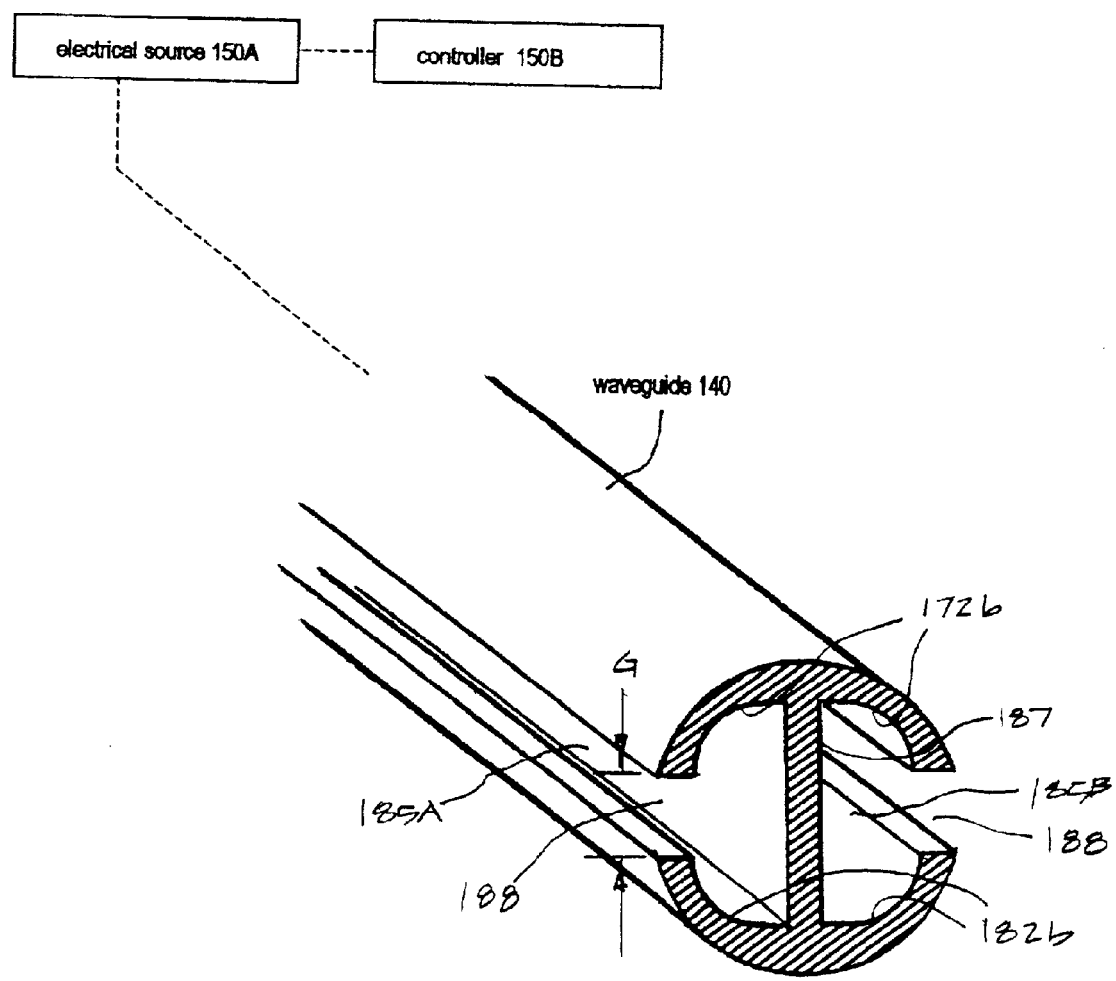
FIG. 5 is a sectional view of the waveguide portion of the ultrasonic energy transmission assembly of FIG. 4 taken along line 5—5 of FIG. 4.

As shown in FIGS. 2 and 7, the jaw elements 120A and 120B in this embodiment define outward partly-round engagement surfaces indicated at 172*a* and 172*b*, respectively, that are adapted to contact the cooperating partly-round engagement surfaces 182*a* and 182*b* formed in channels 185A and 185B of waveguide 140 (see FIG. 5). In this exemplary embodiment, tissue cutting functionality also is provided in the waveguide-extension member 140 by means of the sharp distal cutting element 166 (see FIG. 4).

Now turning to FIG. 5, the sectional view of waveguide-extension member 140 shows the functional components and surfaces of the reciprocatable waveguide member. The jaw elements 120A and 120B in this embodiment define outward engagement surfaces indicated at 172*a* and 172*b*, respectively (see FIG. 2). In the embodiment depicted in FIGS. 4 and 5, it can be seen that terminal portion 145 of waveguide 140 has axially-extending left and right channel portions indicated at 185A and 185B with central web portion 187 that are inflexible and shaped to fit over exterior surfaces 172*a* and 172*b* of the jaw elements with very close tolerances. More in particular, the inner engagement surfaces 182*a* and 182*b* of the left and right channels 185A and 185B, respectively, are adapted to engage and contact substantially the entire length dimension D of the jaw's exterior surfaces 172*a* and 172*b* (FIG. 2) as waveguide 140 is slidably moved from a first retracted position toward a second extended position. It is such engagement under very close tolerances between the reciprocatable waveguide and the jaws that allows the elements to function as components of a tuned acoustic assembly.

For example, FIGS. 5 and 7 show a channel 185A at the right side of the instrument (left in view) that has surface portions 182a about its upper and lateral sides that slidably engage surfaces 172a of one sub-element (171a) of jaw element 120A (see FIG. 2). Likewise, FIGS. 5 and 7 show a lower part of the continuous channel 185A with surface portions 182b about the lower and lateral sides of another sub-element (171b) of second jaw element 120B. Of particular interest, the laterally-outward portions of the channel 185A prevents the jaw elements 120A and 120B from flexing laterally outward. It thus can be seen how the waveguide 140 slides over and pivotably flexes the jaws elements toward one another and to an approximated (closed) position (see FIG. 2).

As can be seen in FIGS. 4, 5 and 7, the waveguide 140 defines a longitudinal slot 188 that extends from each channel 185A and 185B to an exterior of the member 140 and receives the tissue margin. The distal end of the slot 188 (see FIG. 4) preferably tapers somewhat from a more open dimension to a tighter dimension to initially allow the waveguide-extension member to slide over engaged tissue. FIGS. 4 and 5 illustrate that the combination of the cross-sections of waveguide 140 and jaw elements 120A–120B define a gap dimension indicated at G between the jaw engagement faces 122A–122B.

Figure 6:
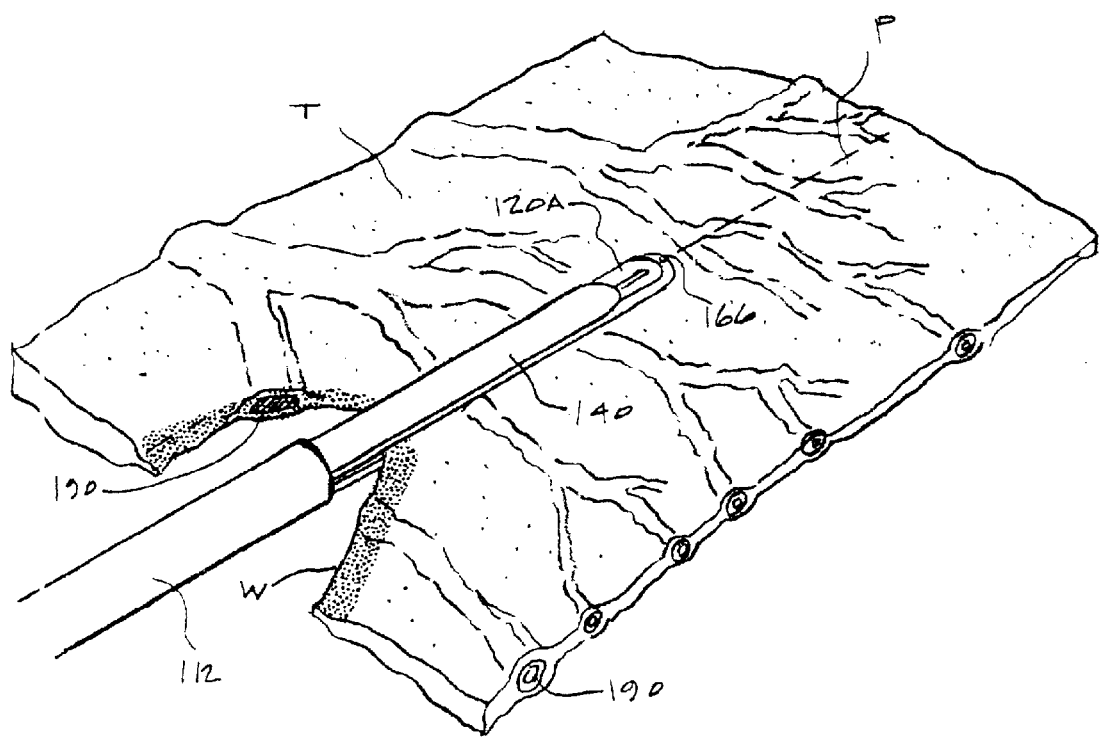
FIG. 6 is a view of instrument of FIGS. 1–3 depicting a method of the invention in transecting and welding the mesentery of a patient including blood vessels therein.

It can be understood from FIGS. 6 and 7 that the rigid waveguide 140 in combination with jaw elements 120A and 120B can apply very high compressive forces over a continuous elongate path in tissue for purposes of tissue welding that would not possible with a conventional jaw-type instrument. It has been found that any conventional jaws cannot provide high compression continuously over the length of elongate jaws since the jaws invariably flex in the preferred small diameters that are used for endoscopic surgeries. The gap G between the jaw's engagement faces 122A–122B preferably is from about 0.05" to 0.0005" for many tissues to create effective welds, wherein the term gap refers to an average dimension between the jaw's engagement surfaces 122A–122B when serrated or impressed with similar tissue-gripping features. More preferably, the gap g is from about 0.01" to 0.001" for most tissues to create an effective weld.

Now turning to FIGS. 6 and 7, the operation and use of the working end 110 of the system in performing a method of the invention can be briefly described as follows. FIG. 6 depicts the waveguide 140 being advanced from a retracted position toward an extended position as it closes the jaws and ramps over the targeted tissue T (mesentery) along a path indicated at p. FIG. 6 shows that the transected tissue margins and blood vessels are sealed by weld W after the jaws and reciprocating member end were advanced along an initial portion of path p. The advancing waveguide 140 closes the jaw elements 120A–120B tightly over the tissue margins as it moves to its extended position. The laterally-outward portions of the waveguide 140 thereby slide over the just-transected tissue margins contemporaneous with the cutting element 166 transecting the tissue. By this means, the transected tissue margins are captured under extreme high compression by the jaws faces on opposing sides of the tissue. The targeted tissue T may be any soft tissue or anatomic structure of a patient's body and is shown in FIG. 6 as mesentery with a plurality of blood vessels 190 therein.

FIG. 7 shows a sectional view of the working end 110 engaging tissue wherein ultrasound energy is delivered to the waveguide 140 which is coupled to the jaw elements to deliver ultrasonic energy from both jaw's tissue-contacting surfaces 122A and 122B to the captured tissue. The ultrasound energy can be delivered contemporaneously with the movement of waveguide 140 from its retracted position to its extended position. Alternatively, the transection of the tissue along path p can be accomplished before activating the ultrasound system to deliver energy to the waveguide 140 and jaws to weld the transected tissue margins. In this embodiment, the tissue transection is performed by a blade-type cutter 166 at the distal end of the waveguide 140, but as will be described below, the cutting functionality can be provided by ultrasonic or electrosurgical cutting means or any other energy-based cutting mechanism.

In an optional embodiment of the handpiece, as depicted in FIG. 1, the ultrasonic assembly 125 and introducer sleeve 112 comprise an assembly that can be selectively rotated with respect to handle 106 by rotation grip 192 in order to allow the physician more control over the orientation of the working end in a particular procedure.

It is contemplated that the reciprocatable waveguide of the invention can operate to deliver energy at any time that the waveguide 140 is advanced even partly over the jaw elements. The waveguide when advanced over the jaw elements to any partly extended position can still acoustically couple sufficiently with the jaws to delivery ultrasonic energy to tissue for purposes of coagulation, sealing or welding of small blood vessels. Thus, it is contemplated that the jaw structure can be used effectively in surgeries as a general tool for grasping, dissecting and cauterizing tissues in cases when the physician elects not the apply full compressive forces against the captured tissue, as is preferred for creating an effective weld in large blood vessels. The scope of the invention further is intended to include any working end that carries paired jaw elements that are both energized by means of a reciprocatable waveguide in contact with such paired jaw elements.

In the above description of the invention and its method of use explain how the sharp blade member 166 at the distal end of the reciprocating waveguide 140 transects the engaged tissue. It should be appreciated that the ultrasonic energy transmitted by waveguide 140 also causes ultrsonic vibration in the distal blade member 166 and therefore a method of the invention includes the ultrasonic-assisted transection of cutting tissue at the distal end of the reciprocating waveguide. In a method of operation, the system can ultrasonically drive the waveguide at a first selected frequency that is optimized for tissue transection as the jaws elements are closed. Thereafter, the system can automatically or manually change to drive the waveguide at a second selected frequency that is optimized for tissue welding as the jaws elements apply full compressive pressures to the engaged tissue.

Another embodiment of the instrument (not shown) provides a central bore in a primary reciprocating waveguide 140 that carries a secondary ultrasonic waveguide therein that has an independent transducer portion. This secondary waveguide is coupled to the distal tissue-cutting element. In this embodiment, the secondary ultrasonic waveguide can be driven at a selected frequency that is optimized for tissue transection by the distal blade element. The primary waveguide can be driven at a selected frequency that is optimized for tissue welding by the jaw elements, either contemporaneous with energy delivery to the secondary waveguide or following closure of the jaws.

2. Type "B" system for sealing and transecting tissue. The working end of a Type "B" system 200 is shown in FIGS.

Figure 8A:
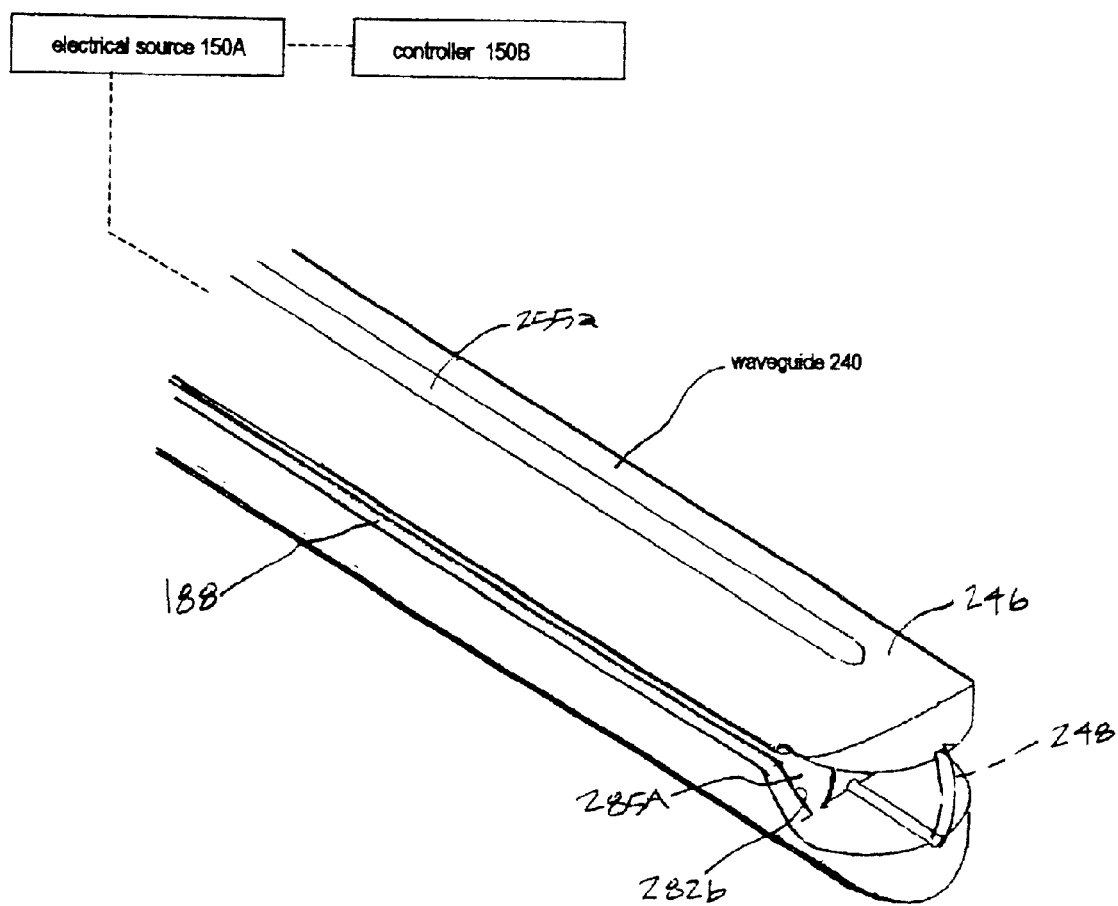
FIG. 8A is a working end of a waveguide of a Type "B" system of the invention showing a cutting electrode.
Figure 8B:
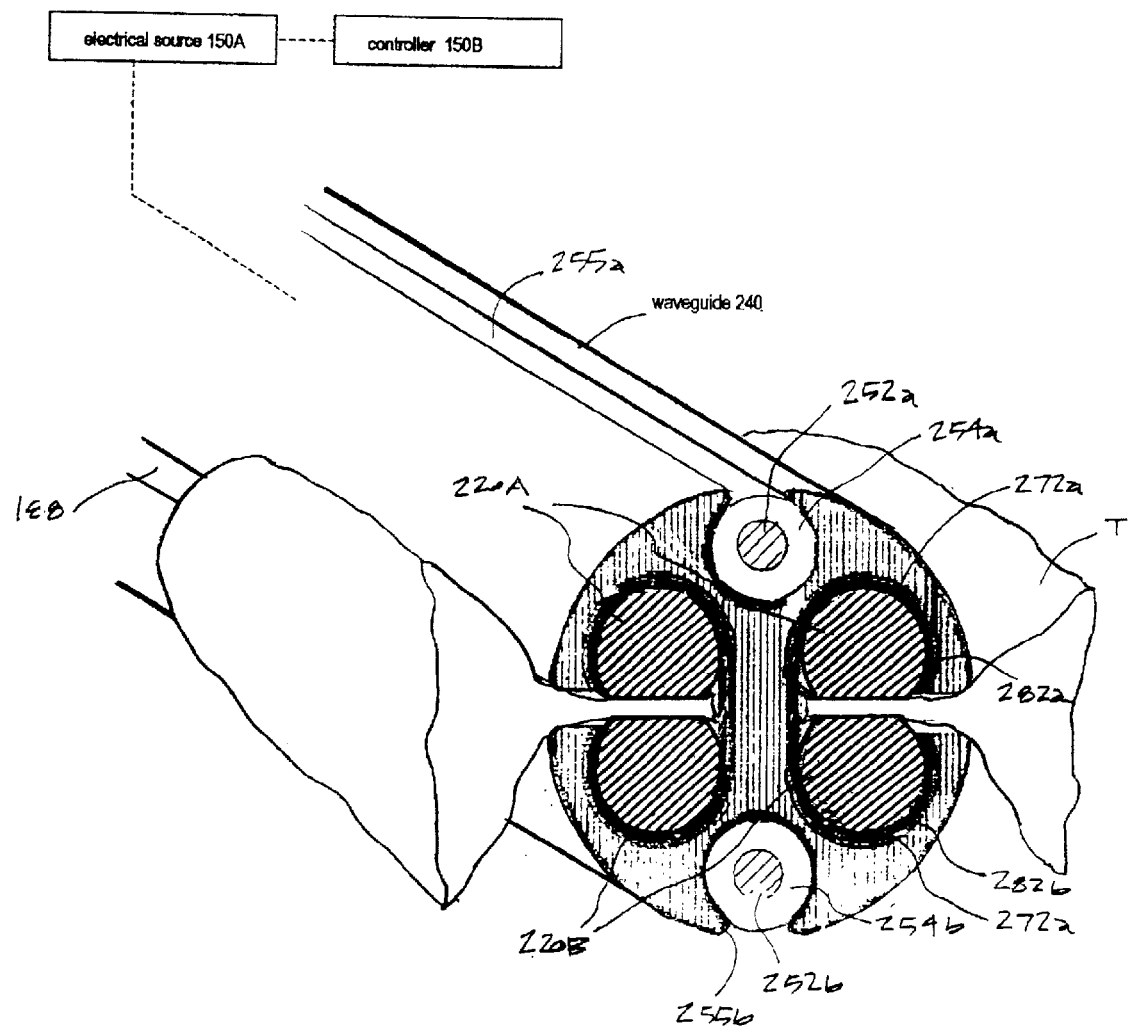
FIG. 8B is a sectional view of the working end FIG. 8A depicting a method of the invention in welding tissue.

8A–8B, which functions substantially the same as the Type "A" embodiment with the exception that jaw elements 220A and 220B cooperate with reciprocating waveguide 240 that has its distal end 246 carrying a cutting electrode 248 (phantom view). The electrode 248 can operate in a mono-polar (or bi-polar) mode for tissue cutting as is known in the art and is coupled to an electrical source 250A and controller 250B. Referring to FIG. 8A, the electrode 248 preferably is detachable from the distal end of waveguide 240 to provide a reusable waveguide. FIG. 8B shows that electrical leads 252a and 252b have insulation layers 254a and 254b, respectively, and are carried in axial grooves 255a and 255b in the waveguide to couple the electrode 248 to the electrical source 250A.

The embodiment of FIGS. 8A–8B shows that jaw elements 220A and 220B have almost fully round cross-sections that can potentially simplify the manufacture of such jaw elements from a wire form for small diameter working ends. The jaw elements 220A and 220B again define upper and lateral side engagement surfaces 272a and 272b that slidably engage surfaces 282a and 282b of continuous channels 285A and 285B within the reciprocating waveguide 240. The continuous engagement of the lateral outward portions of channels 285A and 285B and jaw elements 220A and 220B again insure that the jaws elements cannot flex laterally outward as the jaws are closed. In all other respects, the system operates as described previously.

Figure 9:
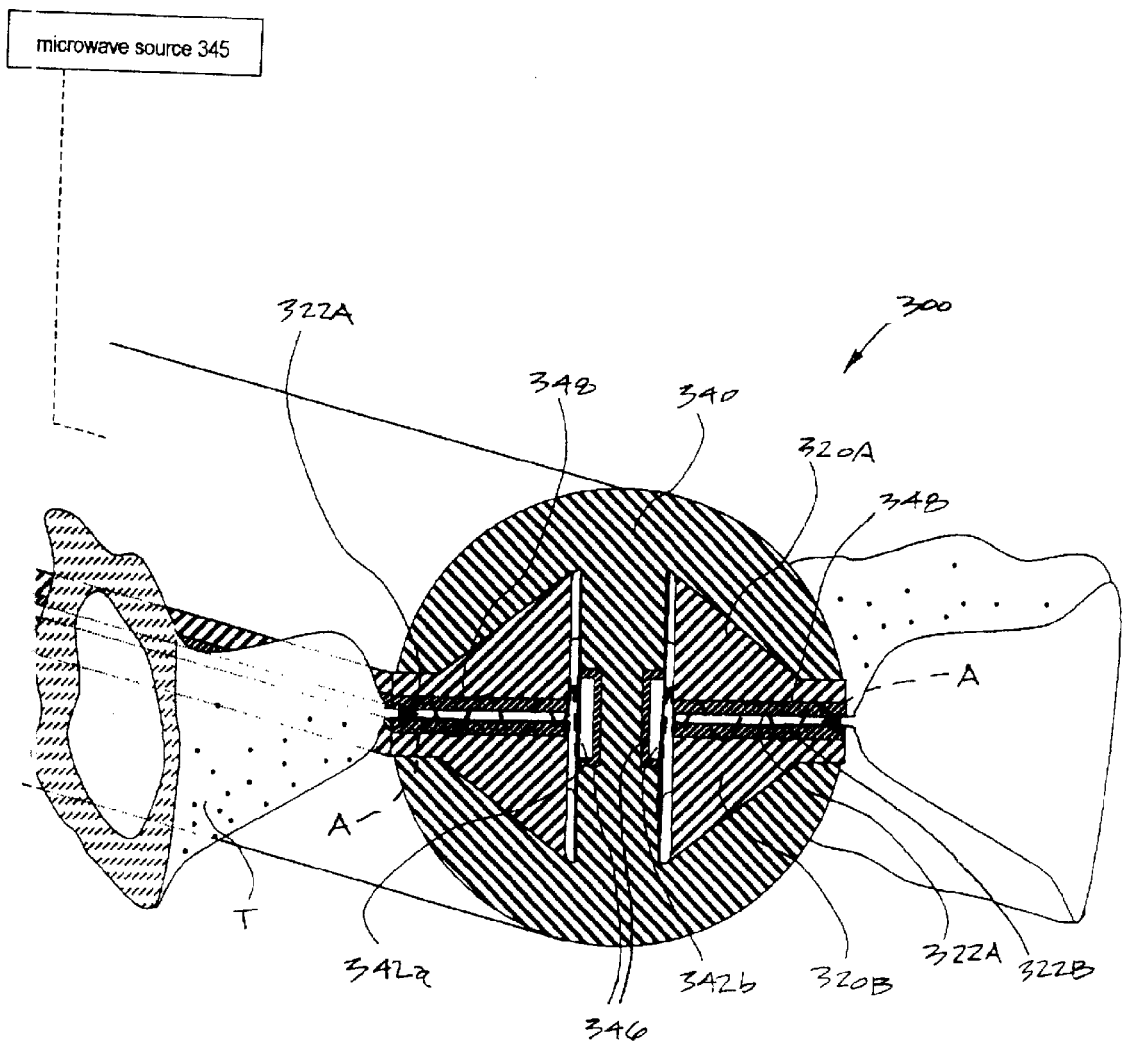
FIG. 9 is a working end of a Type "C" system showing a reciprocatable member that carries a microwave energy source that can couple energy directly to engaged tissue and optionally to surfaces of the jaw elements that are of microwave responsive materials.

3. Type "C" system for sealing and transecting tissue. The working end of an exemplary Type "C" system 300 is shown in FIG. 9, which differs from the Type "A" embodiment in the form of energy coupled to the working end. The jaw closing functionality is substantially the same as the previously described embodiments. Thus, one key aspect of the method of the invention again relates to the high compressive pressures applied to tissue captured between the jaw elements 320A and 320B while delivering thermal energy from the jaw faces 322A and 322B to tissue.

As can be seen in FIG. 9, the central reciprocating member indicated at 340 carries elongate right-side and left-side microwave emitters or antennas 342a and 342b coupled to a remote microwave source 345. The antennas 342a and 342b are separated from the body of reciprocating member 340 by insulating layers 346. It can be easily understood how microwave propagation from elongate antennas 342a and 342b proximate to the transected tissue can be absorbed by tissue engaged between the opposing jaw portions to create thermal effects therein. In a preferred embodiment depicted in FIG. 9, the jaw faces 322A and 322B carry an additional functional surface layer 348 of a microwave absorbing material. In operation, even a substantially thin surface layer 348 of microwave responsive material can absorb microwave energy (indicated by arrows A in FIG. 9) and thus be elevated in temperature to thereby conduct thermal energy to the tissue T engaged therebetween.

It is further contemplated that the reciprocating member 340 can carry first and second means of thermal energy deliver, for example, a first acoustic energy delivery means as described previously together with a second microwave energy delivery means as described just above. The reciprocating member 340 can again be reusable and adapted for use with a disposable introducer and jaw structure. In such an embodiment, the use of first and second energy sources can provide means for a very rapid ramp-up in tissue temperatures that might not be achievable with energy delivery from any single energy source. In a method of use, the system can thus deliver energy to engaged tissue from the first and second energy sources contemporaneously, or in sequential intervals, or in any combination thereof. Further, any system of the invention in can carry thermocouples proximate to the jaw faces that are connected to feedback circuitry and a coupled to an electrical source for sealing tissue.

Figure 10:
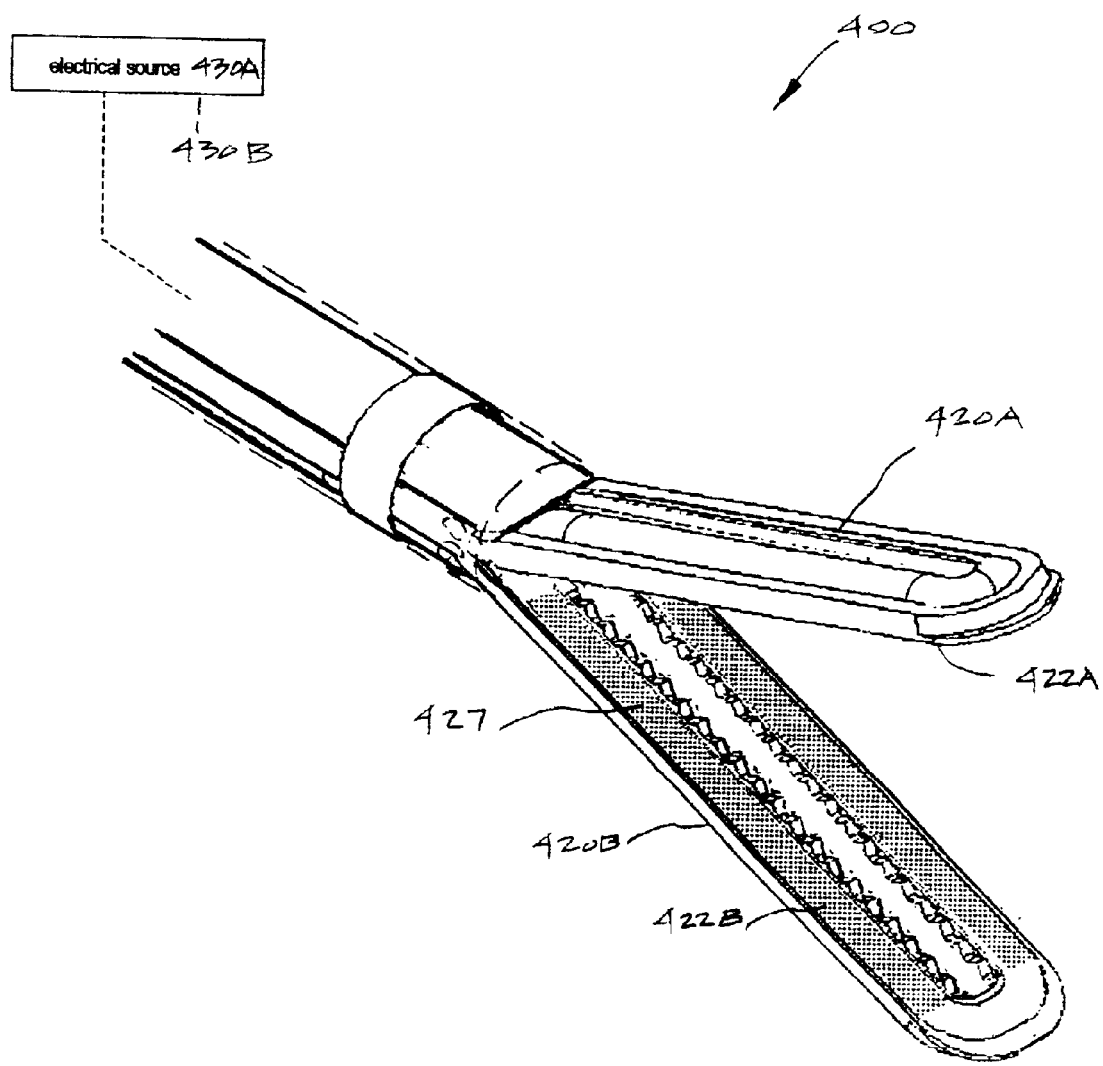
FIG. 10 is an alternative embodiment of Type "C" working end showing jaw elements carrying resistive surface layers coupled to an electrical source.

FIG. 10 illustrates another embodiment of a Type "C" working end 400 which carries first and second energy delivery means—this time with the second energy delivery means directly coupled to the jaws rather than the reciprocating member. The instrument working end of FIG. 10 again applies high compressive pressures to tissue captured between jaw elements 420A and 420B. As described previously, acoustic energy is transmitted by central waveguide member 440 that couples the energy to the jaw elements and jaw faces 422A and 422B. However, it is further contemplated the second means of thermal energy delivery can comprise at least one jaw face carrying a selected conductive material 427 that is resistively heated by electrical source 430A and controller 430B. Electrical leads within the jaw elements couple the conductive material 427 to the source 430A. Such resistive heating of the jaw faces can accelerate thermal energy delivery to tissue engaged under high compression in combination with acoustic energy delivery (or independently). In this embodiment, the jaws can carry thermocouples connected to feedback circuitry and controller 430B to modulating energy delivery from the first and second energy sources.

The high compression jaw structure of the working end can be utilized with other methods of energy deliver to the jaw faces. For example, as generally disclosed in co-pending U.S. patent application Ser. No. 09/792,825 filed Feb. 24, 2001 titled Electrosurgical Working End for Transecting and Sealing Tissue, the reciprocating member and/or the jaw elements can be configured with bi-polar (or mono-polar) electrodes coupled to an electrical source for sealing tissue.

In another embodiment (not shown), the invention can provide a first jaw element that is fixedly coupled to the distal end of the elongate introducer member wherein the introducer is a first waveguide coupled to an ultrasound source. The instrument can carry a reciprocatable member that functions exactly as described above as a second waveguide as well as functioning to close the (moveable) second jaw element and to couple acoustic energy to the second jaw. Each jaw element then can deliver acoustic energy to provide a plurality of operating modes. For example, one jaw can be used to apply coagulating energy and the other jaw can apply cutting energy.

In another embodiment (not shown), the invention can provide a laser or other intense light source that is coupled by optical fibers to emitters in the jaw faces for delivering energy to the engaged tissue.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. An ultrasonic surgical instrument for delivering energy to tissue, comprising: an introducer; first and second elongate jaw elements carried at a distal working end of said introducer; and an ultrasonic waveguide reciprocatably coupled to said introducer; wherein said waveguide defines receiving channels therein with engagement surfaces that engage cooperating exterior engagement surfaces of said jaw elements to thereby move the jaw elements from a spaced apart position to an approximated position as the waveguide moves from a first retracted position and to a second extended position relative to said introducer.

2. The surgical instrument of claim 1 further comprising at least one piezoelectric element coupled to the waveguide thereby providing an ultrasonic energy source.

3. The surgical instrument of claim 2 wherein said at least one piezoelectric element is fixedly coupled to the waveguide and reciprocatable therewith.

4. The surgical instrument of claim 1 wherein said waveguide and said first and second jaw elements comprise portions of a tuned acoustic assembly.

5. The instrument of claim 1 wherein the tolerance between said cooperating engagement surfaces is less than about 0.01 inches to thereby insure acoustic coupling between the waveguide and the jaw elements.

6. A surgical instrument for delivering energy to tissue, comprising:
an introducer member having a working end that defines opposing jaw portions for engaging tissue;
a reciprocatable ultrasonic waveguide carried by said introducer member;
wherein at least one moveable jaw portion and the reciprocatable waveguide define respective first and second engagement surfaces for engaging one another to move said at least one jaw portion toward a closed position;
wherein in the closed position, the second engagement surface of the reciprocatable waveguide engages the first engagement surfaces of said at least one jaw portion substantially from a proximal end to a distal end of said jaw portion;
at least one energy delivery mechanism coupled to said working end for delivering energy to tissue; and
wherein the energy delivery mechanism comprises an ultrasound source coupled to at least one of said jaw portions.

7. A surgical instrument for delivering energy to tissue, comprising:
an introducer member having a working end that defines opposing jaw portions for engaging tissue;
a reciprocatable ultrasonic waveguide carried by said introducer member;
wherein at least one moveable jaw portion and the reciprocatable waveguide define respective first and second engagement surfaces for engaging one another to move said at least one jaw portion toward a closed position;
wherein in the closed position, the second engagement surface of the reciprocatable waveguide engages the first engagement surfaces of said at least one jaw portion substantially from a proximal end to a distal end of said jaw portion;
at least one energy delivery mechanism coupled to said working end for delivering energy to tissue; and
wherein the energy delivery mechanism comprises an ultrasound source coupled to a cutting element.

8. A surgical instrument for delivering energy to tissue, comprising:
an introducer member having a working end that defines opposing jaw portions for engaging tissue;
a reciprocatable ultrasonic waveguide carried by said introducer member;
wherein at least one moveable jaw portion and the reciprocatable member define respective first and second engagement surfaces for engaging one another to move said at least on jaw portion toward a closed position;
wherein in the closed position, the second engagement surface of the reciprocatable waveguide engages the first engagement surfaces of said at least one jaw portion substantially from a proximal end to a distal end of said jaw portion;
at least one energy delivery mechanism coupled to said working end for delivering energy to tissue; and
wherein the reciprocatable waveguide and jaw portions source comprise portions of a tuned acoustic assembly.

9. An ultrasonic surgical instrument for delivering energy to tissue, comprising:
an introducer portion;
paired jaw elements carried at a distal end of said introducer portion wherein outwardly facing portions of at least one jaw element define a first engagement plane;
a reciprocatable member carried within said introducer portion, wherein at least one channel in said reciprocatable member defines a second engagement plane that slidably engages said first engagement plane to thereby move at least one jaw element toward a closed position as said reciprocatable member moves from a first retracted position and a second extended position; and
an ultrasound source operatively coupled to the reciprocatable member wherein said reciprocatable member comprises a waveguide.

10. The surgical instrument of claim 9 wherein said reciprocatable member and at least one jaw element comprises a portion of a tuned acoustic assembly.

11. The surgical instrument of claim 9 further comprising an ultrasound source coupled to a cutting member carried at a distal end of said reciprocatable member.

12. A method of delivering energy to tissue, comprising: providing an introducer carrying opposing jaw portions that define a first engagement plane together with a reciprocatable waveguide member with channel portions therein that define a second engagement plane for slidably engaging said first engagement plane to move the jaw portions from a spaced apart position to an approximated position; and engaging tissue between the opposing jaw portions in the approximated position; and delivering acoustic energy to said reciprocatable waveguide member wherein said acoustic energy is coupled to at least one jaw portion and thereafter coupled to said tissue engaged by the opposing jaws portions.

13. The method of claim 12 wherein the delivering step delivers acoustic energy to said reciprocatable waveguide member wherein said acoustic energy is coupled to both opposing jaw portions and thereafter to opposing sides of the engaged tissue.

14. The method of claim 12 wherein the delivering step delivers acoustic energy to said reciprocatable waveguide member wherein said acoustic energy is coupled to a cutting member at the a distal end of the reciprocatable waveguide.

15. A surgical instrument for delivering energy to tissue, comprising:
an introducer having a working end that defines opposing jaw portions for engaging tissue;
a reciprocatable member carried by within said introducer;
wherein at least one jaw portion is moveable and defines a first engagement surface and wherein the reciprocatable member defines a second engagement surface that engages said first engagement surface to move said opposing jaw portions toward a closed position;

an energy delivery source coupled to said reciprocatable member for delivering energy to tissue engaged between said opposing jaw portions; and at least one antenna carried by said reciprocatable member and wherein the energy delivery mechanism comprises a microwave source coupled to said at least one antenna.

16. A surgical instrument for delivering energy to tissue, comprising:

an introducer having a working end that defines opposing jaw portions for engaging tissue;

a reciprocatable member carried by within said introducer;

wherein at least one jaw portion is moveable and defines a first engagement surface and wherein the reciprocatable member defines a second engagement surface that engages said first engagement surface to move said opposing jaw portions toward a closed position;

an energy delivery source coupled to said reciprocatable member for delivering energy to tissue engaged between said opposing jaw portions;

at least one antenna carried by said reciprocatable member and wherein the energy delivery mechanism comprises a microwave source coupled to said at least one antenna; and a tissue-contacting surface layer of the opposing jaws portions made of a microwave responsive material that is elevated in temperature in response to selected parameters of microwave transmission from said at least one antenna.

17. A surgical instrument for delivering energy to tissue, comprising:

an introducer having a working end that defines opposing jaw portions for engaging tissue;

a reciprocatable member carried by within said introducer;

wherein at least one jaw portion is moveable and defines a first engagement surface and wherein the reciprocatable member defines a second engagement surface that engages said first engagement surface to move said opposing jaw portions toward a closed position;

an energy delivery source coupled to said reciprocatable member for delivering energy to tissue engaged between said opposing jaw portions; and wherein said microwave responsive material comprises a substantially thin layer of a polymer.

* * * * *